United States Patent [19]

Drudik

[11] Patent Number: 5,125,892
[45] Date of Patent: Jun. 30, 1992

[54] DISPENSER FOR STORING AND MIXING SEVERAL COMPONENTS

[76] Inventor: Arnie Drudik, 6870 Somerled, Notre-Dame-De-Grâce, Quebec, Canada, H4V 1V1

[21] Appl. No.: 579,299

[22] Filed: Aug. 14, 1990

[30] Foreign Application Priority Data

May 15, 1990 [CA] Canada .................. 2016870

[51] Int. Cl.⁵ .................. A61M 37/00; A61M 5/24
[52] U.S. Cl. .................. 604/90; 604/89; 604/200
[58] Field of Search .................. 604/82-90, 604/191-192, 199-204, 226

[56] References Cited

U.S. PATENT DOCUMENTS

| | | | |
|---|---|---|---|
| 2,445,477 | 7/1948 | Folkman | 604/87 |
| 2,636,493 | 12/1950 | Lockhart | 604/90 |
| 2,688,966 | 10/1951 | Huber | 604/90 |
| 2,707,466 | 5/1955 | Haskins et al. | 604/201 |
| 2,869,543 | 1/1959 | Ratcliff et al. | 604/90 |
| 3,659,749 | 4/1972 | Schwartz | 604/87 |
| 3,835,835 | 9/1974 | Thompson et al. | 604/191 |
| 4,116,240 | 9/1978 | Guiney | 604/191 |
| 4,148,316 | 4/1979 | Xanthopoulos | 604/199 |
| 4,405,317 | 9/1983 | Case | 604/90 |
| 4,464,174 | 8/1984 | Ennis | 604/90 |
| 4,512,768 | 4/1985 | Rangaswamy | 604/191 |
| 4,563,174 | 1/1986 | Dupont et al. | 604/89 |
| 4,957,637 | 9/1990 | Cornell | 604/191 |

FOREIGN PATENT DOCUMENTS

| | | | |
|---|---|---|---|
| 766545 | 9/1967 | Canada | 128/82 |
| 888333 | 12/1971 | Canada | 128/82 |
| 891356 | 1/1972 | Canada | 217/9 |
| 894352 | 2/1972 | Canada | 128/85 |
| 1001032 | 12/1976 | Canada | 128/84 |
| 1185858 | 4/1985 | Canada | 128/84 |
| 1262327 | 10/1989 | Canada | 128/84 |
| 8903698 | 5/1989 | World Int. Prop. O. | 604/191 |

Primary Examiner—C. Fred Rosenbaum
Assistant Examiner—Mark Bockelman
Attorney, Agent, or Firm—Robert Brouillette

[57] ABSTRACT

The invention relates to a plural-compartment dispenser for storing and mixing several components at least one of them a liquid, and in particular to a dispenser comprising a barrel, a plunger, a needle or means to connect same, finger grip or means to connect same, a stopper placed in the barrel between the needle and the plunger, said stopper having a hollow dilated central cavity open proximally and distally by apertures, said proximal aperture being releasably sealed by a bounded or fitted pressure activated blow plug.

9 Claims, 5 Drawing Sheets

DISPENSER FOR STORING AND MIXING SEVERAL COMPONENTS

FIELD OF THE INVENTION

This invention relates to a dispenser for storing and mixing several components. Particularly, this invention relates to such dispenser that comprises many compartments for mixing at least two components.

BACKGROUND OF THE INVENTION

Many pharmaceutical preparations are unstable when admixed in their carriers thus exhibiting substantially reduced potency and shelf-life, and the state of nature of many polymers and amalgamates necessitates separation into their component parts, until immediately prior to use.

In the case of plural component medications, such as vaccinations, liquid diluents and solid lyophilized components are maintained in separate glass vials with pierceable rubber stoppers. Preparation necessitates a lengthy mixing procedure wherein the stopper of the diluent vial is first pierced with a sterile needle and syringe, and the diluent withdrawn into the syringe. The needle is subsequently withdrawn from the first and inserted in to the second vial and the diluent injected thereto. The medication is admixed and withdrawn into the syringe for injection. In the case of most vaccinations which are typically given by the intramuscular or subcutaneous route, injection procedure requires that the plunger of the syringe be withdrawn slightly after insertion of the needle into the patient. If at that time the hypodermic has been placed into a blood vessel, blood will be aspirated into the syringe. This withdrawal test allows replacement of the needle to a nonintravascular site. This test is likewise performed to confirm intravascularity when a mixture is to be given intravascularly.

The inherent problems of said procedure include considerable expense in the form of: a lengthy procedure, high cost of separate containerization, storage and refrigeration, and the generation of a substantial quantity of medical waste, its problematic disposition and the consumption of resources, in a time where conservation is of particular importance.

Furthermore, repeated insertion and retraction of the sterile needle into the vial stoppers, which are externally unclean and contaminated with microbial organisms increases greatly the risk of contamination of a sterile medical preparation with external environmental contaminants.

Additionally, foreign body contamination by small rubber particles cut from the vial stoppers by the razor sharp bevelled needle, upon insertion, represents a hazard, as these may be injected along with the medication into the patient.

Those skilled in the prior art will recognize this similar disadvantage as seen with prior art apparatuses using pierceable or bursting diaphragms.

Solowey, in Canadian Pat. No. 891,356, teaches the use of a bursting diaphragm wherein a cap-like stopper plug with a bursting bottom is ruptured by pressure generated by a specially designed plunger which inserts into said cap in a male/female interaction, said cap then depressed with the plunger to expel the syringe contents.

The possibility for the ruptured membrane to dislodge and clog up the distal syringe aperture or enter the patient parenterally, is recognized. Said special plunger further necessitates complex specific manufacturing and limits expulsion due to its flat bottom.

Similar disadvantages are recognized with bulb type expulsion systems. Williams, in Canadian Pat. No. 766,545, teaches the use of a bulb type syringe which requires a screwing action and bursting of a diaphragm. Notwithstanding the complex thread machining, the shortcomings of inaccurate dosage are recognized.

Similarly, the prior art utilizing inserts may minimize the accuracy of dosage quantity delivered.

Of the various types of plural compartment containers taught in the patents, bypass type syringes require the movement of a partition into a bypass area, wherein a liquid phase is forced around said partition by the action of a plunger, so as to effect admixing.

There exists however, with regards to the herein above mentioned, a tendency toward a variety of disadvantages which include, a tendency for entrapment of medication at the bypass zone with retention of large residual volumes of medication in the syringe; a reverse propulsion of contents and more difficultly performed withdrawal test.

For instance, Canadian Pat. No. 894,352 (Walecka) utilizes a stopper and plunger that encases two compartments which communicate via an enlargement in the syringe body (bypass). As the plunger is depressed, the translation force moves said stopper into the enlargement or bypass zone. Disadvantageously, as the stopper passes the bypass zone enlargement site entering an area of normal diameter, it thereby seals off the distal compartment and precludes the inclusion of the entire volume of proximal medication in dispensation. Additionally, a fixed bypass fixes the volume of proximal and distal compartment sizes necessitating a specific syringe for each specific medication volume.

Szwarc, in Canadian Pat. No. 1,262,327, teaches a bypass arrangement wherein a slight enlargement placed laterally on the syringe body, sealed proximally by a movable stopper. As in the herein above mentioned bypass arrangement, fluid flows preferentially around the bypass until said stopper engages the distal non-bypass zone. At or about that point is encountered a tendency for retropulsion of a portion of the medical volume in a proximal or backward direction out of the syringe barrel, potentially aerosolizing harmful biologics or vaporous chemicals. To prevent said extra-syringation of medication, complex flanges must be included to catch the spilling medication.

It is known from the prior art that utilizing a cannular bypass like in Canadian Pat. No. 1,185,858 (Lissenburg et al), may create a tendency for difficult visualization of blood during the withdrawal test.

Zackheim, in Canadian Patent No. 888,333, teaches a valve seated across a syringe body propped up by a ledge. Upon depression of a plunger, said valve is moved off its ledge by tilting into a perpendicular orientation with respect to its original position, so as to effect fluid bypass and admixing of components. A tendency for said valve to remain perpendicular, thereby precluding expulsion of a fluid column approximately equal to the perpendicular height of said valve as it becomes entrapped at the distal inner syringe barrel in a perpendicular fashion by the plunger, is recognized.

Furthermore, smooth ejection is precluded, in that the ledge must be bypassed by the syringe plunger. This may lead to patient discomfort and pain due to the cutting action of the razor sharp, bevelled, moving needle in the patient's dermis or muscle, and hazard in the case of Veterinary Medicine, wherein rapid painfree injection is necessary in intractable animals.

Other prior valve sealing apparatuses include multi-component syringes (Canadian Patent No. 1,001,032) which require costly manufacturing and precision design.

Dupont et al, in U.S. Pat. No. 4,563,174, teach a syringe separated into parts by a complex rotatable seal valve double plunger system. The necessary precision and material usage makes this arrangement unsuitable for single use, being cost prohibitive and generating undue medical waste.

The syringe apparatuses herein above eluded to, represent plural-compartment containers but none have adequately addressed the need for a simple, cost effective, low wastage, reliable pluro-compartment mixing dispensing container. Doctors, and especially veterinary doctors, strongly recognize the need for a pluro-compartment mixing dispensing container which addresses the hereto mentioned medical requirements, while adaptable to current manufacturing procedures and current theories of conservation.

OBJECTS OF THE PRESENT INVENTION

The object of the instant invention is to adequately address the need for a simple, cost effective, low wastage, reliable, pluro-compartment mixing dispensing container syringe which lends itself to all the herein mentioned medical requirements, while adaptable to current manufacturing procedures and current theories of environment and resource conservation.

It is a general object of the present invention to provide a dispenser arrangement for use particularly in packaging and subsequent dispensing of fluid-flowable materials.

SUMMARY OF THE INVENTION

The present invention generally provides a partitioning stopper for a two compartment syringe assembly for dispensing a liquid medication derived from the mixing of a first and a second component, one of the components being a liquid, the assembly having a cylindrical medication barrel having a forward (i.e. distal) medication delivery end and a rearward (i.e. proximal) end and an axially slidable plunger for closing off the rearward end of the barrel, the plunger being disposed in fluid tight engagement in the barrel, the partitioning stopper being separated from the plunger being configured for dividing the barrel into the two compartments, the partitioning stopper being configured for slidable fluid tight engagement in the barrel, the stopper having a fluid passageway extending axially therethrough, the fluid passageway having a pop-out blow plug disposed for fluid tight engagement therein, the blow plug being displaceable, so as to unblock the fluid passage, under fluid pressure, as induced by movement of the plunger, the partitioning stopper being configured for forward displacement by abutting contact with the plunger as the plunger undergoes forward movement, the partitioning stopper being characterized in that the stopper is of a resilient material, the fluid passageway consists of a first rearward (i.e. proximal) opening and a second forward (i.e. distal) opening connected to and spaced apart by a fluid bypass chamber, the bypass chamber having a forward (i.e. distal axial end wall and a rearward (i.e. proximal) axial end wall, the first opening being defined by the rearward axial end wall and the second opening being defined by the forward axial end wall, the pop-out blow plug is sized larger than the first and second openings and smaller than the bypass chamber, and the pop-out blow plug releasably blocks one of the first and second openings, the opening blocked by the blow plug being defined by a respective resilient axial end wall such that, under the above mentioned pressure, the end wall deflects into the bypass chamber and the blow plug is dislodged from the opening into the fluid bypass chamber thereby allowing for bypass flow of liquid from one compartment through the partition stopper and into the other compartment.

The present invention, in particular, provides a two compartment syringe assembly for dispensing a liquid medication derived from the mixing of a first and a second component, one of the components being a liquid, the assembly having a cylindrical medication barrel having a forward (i.e. distal) medication delivery end and a rearward (i.e. proximal) end, an axially slidable plunger for closing off the rearward end of the barrel, the plunger being disposed in fluid tight engagement in the barrel, a partitioning stopper being separated from the plunger for dividing the barrel into the two compartments, the stopper being slidably disposed in fluid tight engagement in the barrel, the stopper having a fluid passageway extending axially therethrough, a pop-out blow plug disposed in fluid tight engagement in the fluid passageway, the blow plug being displaceable, so as to unblock the fluid passage, under fluid pressure, as induced by movement of the plunger, the partitioning stopper being forwardly displaceable by abutting contact with the plunger as the plunger undergoes forward movement, characterized in that the stopper is of a resilient material, the fluid passageway consists of a first rearward (i.e. proximal) opening and a second forward (i.e. distal) opening connected to and spaced apart by a fluid bypass chamber, the bypass chamber having a forward (i.e. distal) axial end wall and a rearward (i.e. proximal) axial end wall, the first opening being defined by the rearward axial end wall and the second opening being defined by the forward axial end wall, the pop-out blow plug is sized larger than the first and second openings and smaller than the bypass chamber, and the pop-out blow plug releasably blocks one of the first and second openings, the opening blocked by the blow plug being defined by a respective resilient axial end wall such that, under the above mentioned pressure, the end wall deflects into the bypass chamber and the blow plug is dislodged from the opening into the fluid bypass chamber thereby allowing for bypass flow of liquid from one compartment through the partition stopper and into the other compartment.

In accordance with the present invention, the blow plug may block the first rearward opening and may be displaceable, so as to unblock the fluid passage, under pressure of a liquid component in the compartment disposed between the plunger and the rearward axial end wall, as induced by forward movement of the plunger.

In accordance with the present invention catch means, for the retention of said blow plug, may, if desired, be disposed within the bypass chamber about the second forward opening.

In accordance with the present invention the blow plug may have a concave rearward face. More particularly, the blow plug may have a frusto-conical shape, a concave rearward face and a forward conical base disposed on the bypass chamber interior side of the rearward axial end wall.

In accordance with the present invention the syringe assembly may have
- a barrel which is open proximally and distally and which has a constant diameter in the longitudinal direction and is rotationally symmetrical;
- a plunger which can be moved in the barrel and seal same, to which a plunger shaft can be connected;
- a needle connected to the distal extent of the barrel or means to connect same and;
- a finger grip or means to connect same to the outside of the barrel.

In accordance with the present invention the dimensions of the stopper disposed in the barrel are such that it can be provided in a sealing manner and be moveable between the plunger and the above mentioned needle or needle connection means.

In accordance with the present invention the stopper can have a hollow dilated central cavity open proximally and distally by apertures. Thus, for example, the proximal aperture may be releasably sealed by a bonded or fitted, pressure activated blow plug, being so arranged as to be preferentially responsive to pressure and force conditions on the proximal side thereof, to form a communicating pathway between said proximal and distal compartment as a result of distal deflection of said blow plug into the central cavity, thereby allowing bypass flow through the stopper and into the distal compartment for the admixing of components.

In accordance with the present invention, the assembly is so configured that the holding forces, which act on the stopper in the barrel, are smaller than the force which may be exerted on the plunger during the injection, so that towards the end of the injection, the plunger can push the stopper forward, thereby allowing the injection substance present between the stopper and the distal end to be expelled as completely as possible. Thus the blow plug and stopper may be configured to utilize differential coefficients of friction and/or releasable bonding, to maintain their postures. The stopper may, for example, be (of elastomeric material) radially uniform and sealably and slideably fitted to the inner barrel by virtue of its slightly larger diameter and flexibility and having at least 2 axially spaced ridges separated by a sulcus and maximizing said sealing relationship.

In accordance with the present invention the blow plug may be dislodgeable free from rubber particle generation which may clog or escape the syringe.

DESCRIPTION OF A PREFERRED EMBODIMENT

Herein from, in reference to the distal extent shall be taken to be that end furthest from the user and nearest to the site of dispensation, (i.e. the forward end) and proximal shall be closest to the user (i.e. the rearward end).

Figure 1:
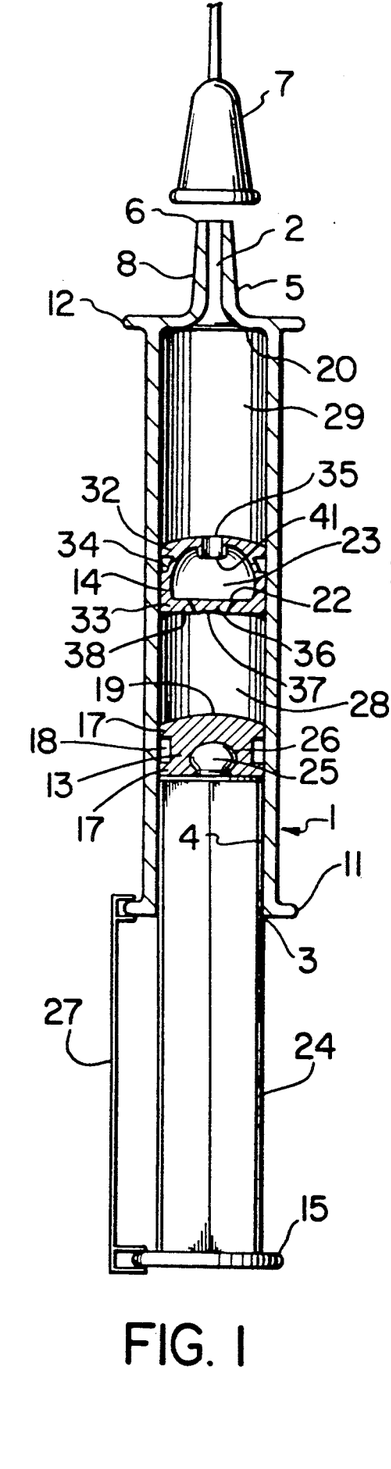
FIG. 1 is a sectional view of a preferred dispenser constructed in accordance with the present invention.

Referring to FIG. 1 of the drawings, a preferred embodiment of the present invention is shown, which is a pluro-compartment storage/mixing/dispensing syringe, with withdrawal test capacity, wherein admixing and dosing of medications or other mixtures is effected.

The said syringe has a longitudinally and rotationally symmetric main barrel 1, uniform and free of radially inward protrusions, open distally and proximally by apertures 2 and 3, and whose inner barrel wall 4, confines both fluids, solids and mixtures thereof.

Barrel 1 which maybe constructed of glass or plastic materials, wherein glass is used to effectuate longer term storage requirements, may for example, be easily moulded from inert transparent plastics such as injection moulded polypropylene. Polypropylene carries substantial benefit like resistance to practically all solvents and medication, low water loss and resistance to sterilization procedures. As seen the barrel 1 has a uniform inner surface free of radial protrusions for smooth operation.

The distal extent 5 of barrel 1 is tapered to a tip 6, to which a hypodermic needle 7, cannula or other suitable conduit may be connected by means of needle or conduit connecting means, such as a luer connector already known in the prior art. The said distal tapered extent 6 comprises a distal and central aperture 2, through which expulsion of mixture may be effected.

Figure 19:
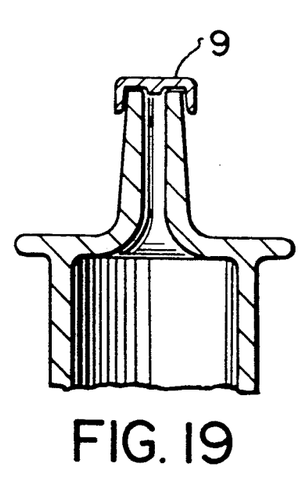
FIGS. 19 and 20 are an exploded sectional view of the dispenser of FIG. 1, showing a closure capability in a flexible attachment cap or a moulded brake away resilient tip.
Figure 20:
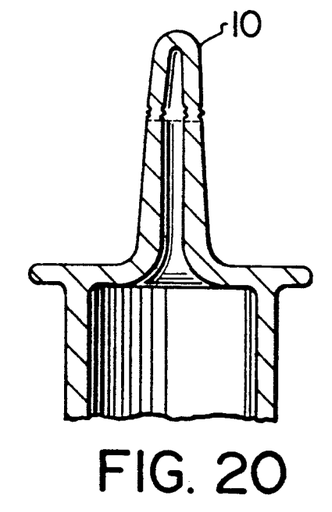

The syringe has a closure capability in a flexible attached cap 9 (FIG. 19) or a moulded break-away resilient tip 10 (FIG. 20), releaseably connected to the tapered tip 6 thereby facilitating an air/fluid-tight seal.

At it's proximal most extent, the barrel 1 has either a circumferential grip or flared finger grips 11 to facilitate holding and activation of the syringe.

Figure 15:
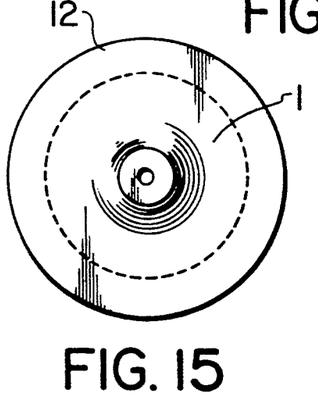
FIG. 15 is a plan view of the distal extremity of the dispenser of FIG. 1, showing one embodiment of the flared finger grips.
Figure 16:
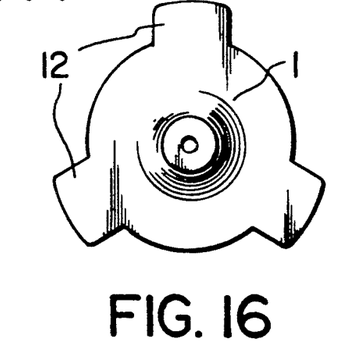
FIG. 16 is a plan view of the distal extremity of the dispenser of FIG. 1, showing another embodiment of the flared finger grips.
Figure 17:
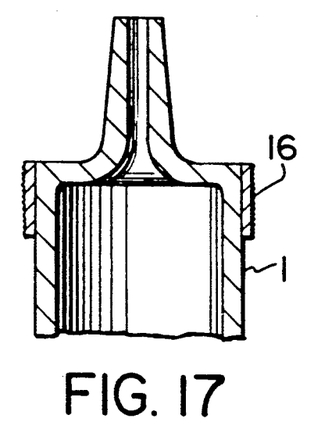
FIG. 17 is an exploded sectional view of the distal extremity of the dispenser comprising roughened finger grips.
Figure 18:
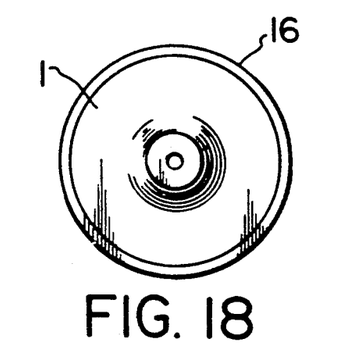
FIG. 18 is a plan view of FIG. 17.

Moreover, at least 2 distally flared finger grips 12 (FIG. 1 and 15) may be included near the tip 6 to facilitate injection, where a slightly increased resistance to expulsion may be encountered due to the presence of both, internal stopper 14 and plunger 13. Nevertheless, the injection stability is improved by the distal grips which have primary importance when close proximity to the needle is required for stable hazard-free injection such as in application to animals in Veterinary Medicine. In the latter, the syringe should be held by the tripodal flared distal finger grips 12 (FIG. 16) close to the injection site, with the plunger shaft grip 15 placed against the palm of the hand of the user in a way that simultaneous counter motion of the palm and fingers results in expulsion of mixture. Alternatively, the syringe barrel may have a raised and roughened finger grip area 16 (see FIG. 17).

Into the proximal aperture 3 of barrel 1, a plunger 13 is fitted in a sliding manner. Said plunger is composed of elastometric material such as medical/pharmaceutical grade rubber and has a diameter slightly larger than the inner diameter of barrel 1. Moreover, the plunger is disposed in an airtight, fluid-tight sealing relation with the inner barrel wall 4 and said plunger has at least two axially spaced ridges 17, separated by a sulcus 18 to maximize the sealing sliding relationship by virtue of a flexible double seal.

Said plunger is convexly curved 19 (FIG. 1) distally so as to apply maximal pressure to the contained fluid column upon axially distal advancement and to permit a more complete evacuation of the substance in the barrel by conforming to the distal terminal inner barrel 20.

Figure 13:
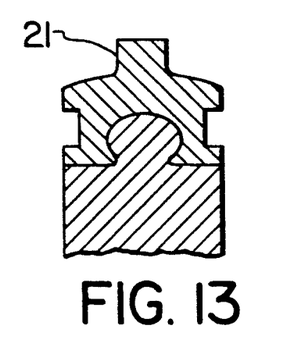
FIG. 13 is a sectional view of another embodiment of the plunger comprising a tip at its distal end.

In another embodiment, plunger 13 comprises a distal tip 21 (FIG. 13) to accommodate a proximal blow plug valve stopper aperture 22 (FIGS. 1-5) in a male/female interaction so as to minimize residual volume in said stopper central cavity 23 (FIGS. 1-5).

Figure 14:
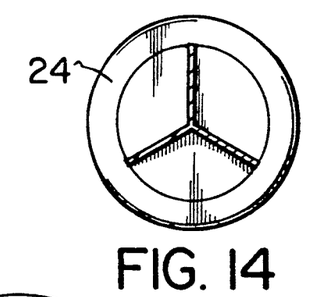
FIG. 14 is a sectional view of tripodal plunger shaft.

Plunger 13 can receive in a male/female interaction, a tripodal plunger shaft 24, which by virtue of its tripodal nature economizes material usage and maximizes shaft strength, affixed thereto by a distally dilated projection 25. Said projection is snapped or screwed into a lipped aperture ridge 26 in the proximal plunger body 13.

Plunger shaft 24 could be preassembled or deployed at the time of usage in a single step, to minimize potential for accidental deployment. If the plunger is deployed, the insertion and depression of the plunger shaft axio-distally results in plunger attachment, mixing of the components inside the barrel 1 and finally, dispensation.

A safety locking clip 27 could be included to prevent accidental depression of the plunger and dispensation of mixture. Said clip should be removeably fitted across proximal finger grip 11 and shaft finger grip 15 so as to immobilize the plunger shaft 24.

A flexible pop-out blow plug valve seal stopper 14, made of rubber, rigid or elastometric material of low chemical reactivity, is positioned axially and slideably in an airtight, fluid-tight engagement into the barrel 1, between the distal extent 20 and the proximally inserted plunger 13. Proximal compartment 28 and distal compartment 29 are thus formed and confine their contents into the inner barrel wall 4; the stopper may be placed at any position relative to distal barrel extend and proximally inserted plunger.

The first proximal content is usually a liquid (L) or diluent and the second distal content a powder, solid (S) or lyophylized powder in the event of vaccines. The distal compartment 29 includes an air space to accommodate the rapidly entering fluid upon the establishment of a communicating pathway between compartments 28 and 29, the so called fluid burst.

Figure 6:
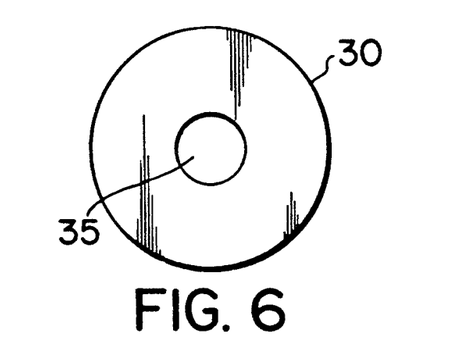
FIG. 6 is a sectional taking along the line II—II of FIG. 4.
Figure 7:
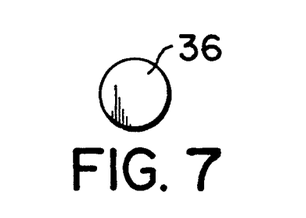
FIG. 7 is a plan view of the blow plug of FIG. 1, in accordance with this invention.

Said stopper 14 has a radially uniform elastic circumference 30 (FIG. 6) and a curved distal extent 31 (FIG. 4), thereby exerting maximal dispensation force upon depression of the plunger and wherein said stopper is of slightly larger diameter than the diameter of inner barrel 4. The stopper 14 is thereby disposed in fluid-tight relationship with the barrel 4, said relationship being maximized by the stopper axially spaced ridges 32 and 33 separated by a sulcus 34. The proximal ridge 33 may be enlarged so as to increase stopper barrel contact area and effect maximal resistance to movement until the time of advancement of said stopper into a fluid containing area with subsequent lubrication of stopper circumferential leading edge and diminution of it's coefficient of resistance at said edge.

Stopper 14 is characterized by a hollow dilated central cavity 23, open proximally and distally by stopper apertures 22 and 35 respectively. The proximal aperture 22 is releaseably sealed by a releaseably connected pressure activated blow plug 36, which by the nature of its releasability acts as a valve, being so arranged as to be preferentially responsive to pressure and force conditions from the proximal side thereof to form a communicating pathway between compartments 28 and 29 as a result of distal deflection of said blow plug 36 into the central cavity 23, thereby allowing bypass flow of liquid from compartment 28 through the proximal stopper aperture 22, through the central cavity 23, by the blow plug 36, through the distal stopper aperture 35 into compartment 29 to effect admixing of material contents (FIG. 3).

Figure 2:
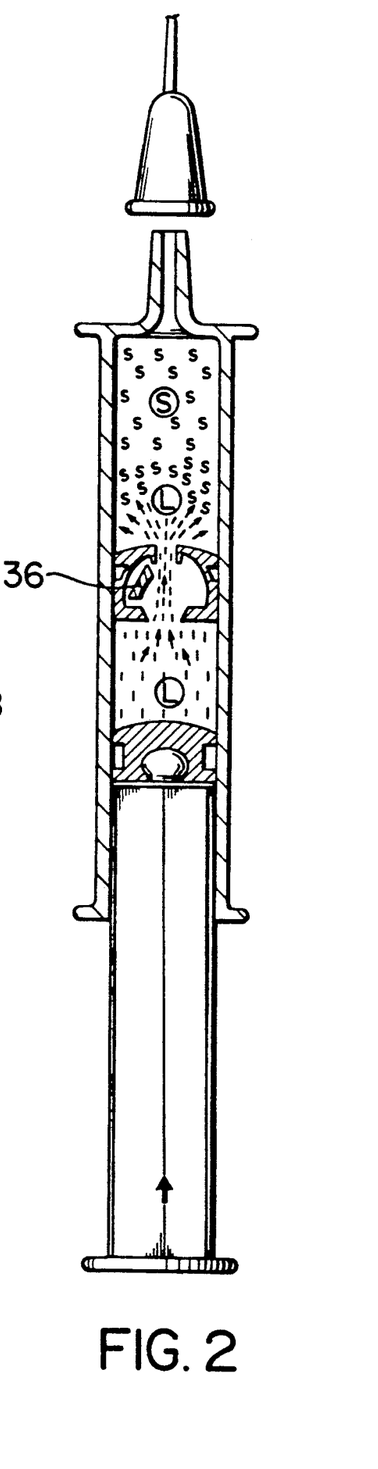
FIG. 2 is a sectional view of the dispenser arrangement of FIG. 1, showing the process for dispensation of mixture.
Figure 3:
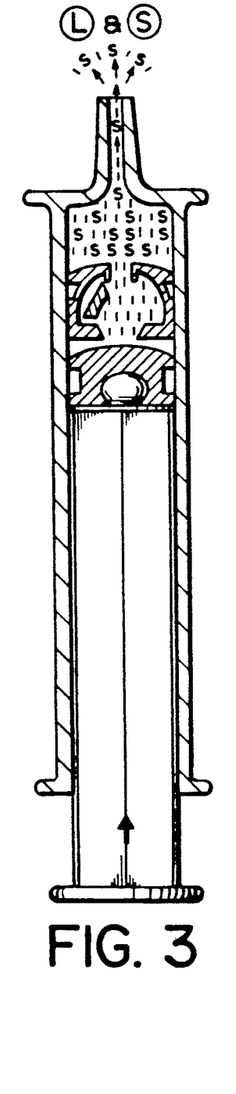
FIG. 3 is another sectional view of the dispenser arrangement of FIG. 1, showing the dispensation of mixture.
Figure 4:
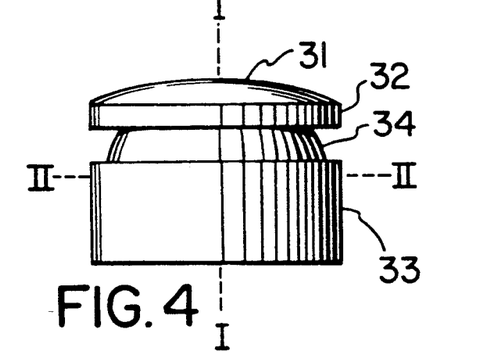
FIG. 4 is a side view of the stopper in FIG. 1.
Figure 5:
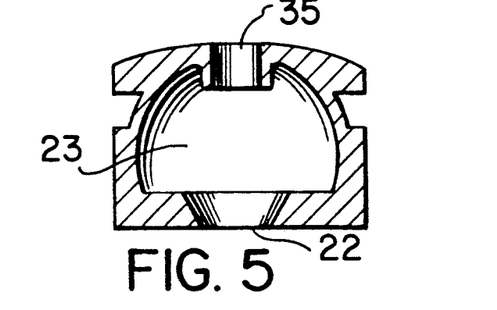
FIG. 5 is a sectional view taking along the line I—I of FIG. 4.

Said force effected by pressing plunger 13 distally and axially into the barrel 4, engages the stopper, initiates unisomous movement of said stopper, fluid and plunger, and dispensation of mixture from the needle (FIGS. 2-3).

A preferred embodiment of the stopper blow plug 36 is characterized by a concave proximal face 37 and diameter smaller than the stopper 14 diameter. The blow plug 36 is releasably bonded or fitted into the proximal stopper aperture 22, utilizing differential coefficients of friction or releasable bonding. Improved force of transmission is effected from plunger 13 to liquid (L), to blow plug 36, when the blow plug has a maximal proximal surface area. Additionally, by virtue of the flexibility resulting from the hollow stopper cavity 23, the stopper 14 may aid in the release of the blow plug 36 owing to deflection of the proximal stopper wall 38 (i.e. the rearward end wall); the stopper by virtue of its flexibility and elastomeric properties aids in the preferential dislodging of said blow plug.

Figure 10:
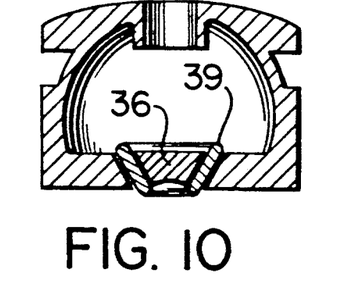
FIG. 10 is a sectional view of a modified stopper comprising sleeves between the proximal upper wall and the blow plug.
Figure 11:
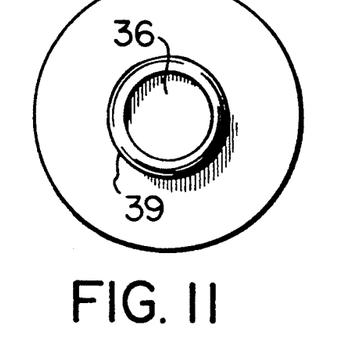
FIG. 11 is a plan view of FIG. 10.

Sleeves 39 (FIGS. 10-11) of hardness and coefficient of friction different from the materials constituting the stopper 14, may be inserted between the blow plug 36 and the proximal stopper walls 38 to provide different resistance and preferential movement of the blow plug 36 and/or said sleeves (over movement of said stopper). Moreover, the sleeves and/or blow plug 36 could be tapered e.g. be conical to effect ease of activation.

Additionally, the ratio of stopper 14 axial length, in comparison to blow plug 36 diameter, and thickness maybe such that the frictional resistance of blow plug 36 toward force conditions in compartment 28 is preferentially overcome before that of said stopper 14, thus allowing admixing by opening of the blow plug valve 36 before movement of said stopper 14. If the said ratio is a limiting factor, a zone of increased frictional resistance along the inner barrel wall 4 may be provided to effect said movement of blow plug 36 preferentially to stopper 14.

The stopper 14 further comprises a catch means to entrap the blow plug 36 within the central cavity 23 and consists of internal distal stopper aperture catch tabs 41 which hold the blow plug within central cavity 23 during admixing and dispensation of mixture. The distal stopper aperture 35 is defined by the forward axial end wall of the cavity 23. The distal stopper aperture 35 is defined by the forward axial end wall of the cavity 23.

Figure 8:
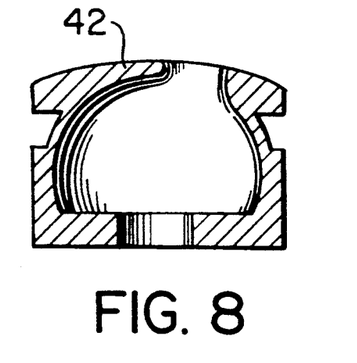
FIG. 8 is a sectional view of a modified stopper, which distal aperture is skewed laterally.

It should be noted that the distal stopper aperture 35 (FIG. 8) could be skewed laterally thereby allowing the distal inner stopper wall 42 to act in a catch means fashion.

Figure 12:
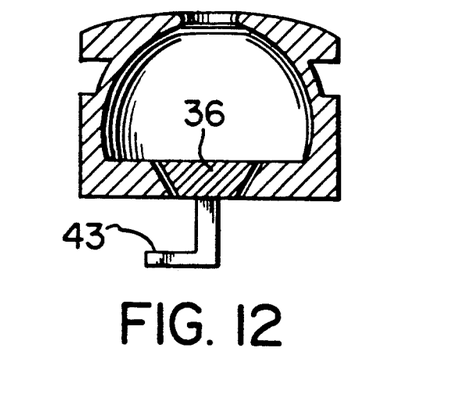
FIG. 12 is a sectional view of a modified blow plug having an anchor.

FIG. 12 shows an alternative embodiment that utilizes a blow plug 36 anchored by a blow plug anchor 43 to preclude movement of said blow plug 36 into compartment 29 while still allowing withdrawal test capabilities and bypass flow.

Figure 9:
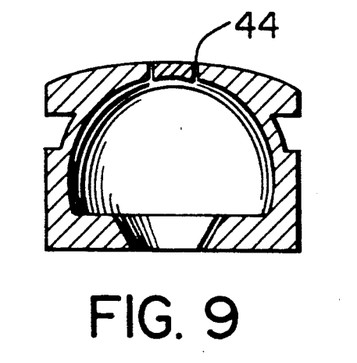
FIG. 9 is a sectional view showing a modified stopper, where the blow plug is placed at the distal end.

Blow plug 36 may also be releaseably positioned at the distal stopper aperture 44 (FIG. 9) and either activated by pressure force exerted by plunger depression and resultant distal expulsion or by vacuum created by proximal plunger 13 withdrawal. In the latter case, the blow plug 36 is pulled into stopper central cavity 23. This vacuum activation applies also to proximal aperture insertion of the blow plug 36.

To those skilled in the art, it will be apparent that stopper 14 is advantageously adaptable to any standard syringe barrel and by variance of the relative position of said stopper 14 with respect to the distal barrel extend 20 and proximally inserted plunger 13 can create advantageously compartments 28 and 29 of various sizes.

It should be understood that the foregoing relates to only a preferred embodiment of the invention which has been shown by way of example, and that it is intended to cover all changes and modification of the example of the invention herein chosen for the purpose of the disclosure which do not constitute departures from the spirit and scope of the invention.

I claim:

1. A two compartment syringe assembly for dispensing a liquid medication derived from the mixing of a first and a second component, one of said components being a liquid, said assembly having
 a cylindrical medication barrel having a forward medication delivery end and a rearward end,
 an axially slidable plunger for closing off the rearward end of said barrel, said plunger being disposed in fluid tight engagement in said barrel,
 a partitioning stopper being separate from the plunger for dividing the barrel into said two compartments, said stopper being slidably disposed in fluid tight engagement in said barrel, said stopper having a fluid passageway extending axially therethrough,
 a pop-out blow plug disposed in fluid tight engagement in said fluid passageway, said blow plug being displaceable, so as to unblock said fluid passage, under fluid pressure, as induced by movement of the plunger,
 said partitioning stopper being forwardly displaceable by abutting contact with said plunger as said plunger undergoes forward movement, characterized in that
 said stopper is of a resilient material,
 said fluid passageway consists of a first rearward opening and a second forward opening connected to and spaced apart by a fluid bypass chamber, said bypass chamber having a forward axial end wall and a rearward axial end wall, said first opening being defined by said rearward axial end wall and said second opening being defined by said forward axial end wall,
 said pop-out blow plug is sized larger than said first and second openings and smaller than said bypass chamber, and
 said pop-out blow plug releasably blocks one of said first and second openings, the opening blocked by the blow plug being defined by a respective resilient axial end wall such that, under said pressure, the end wall deflects into said bypass chamber and said blow plug is dislodged from said opening into the fluid bypass chamber thereby allowing for bypass flow of liquid from one compartment through the partition stopper and into the other compartment.

2. A syringe assembly as defined in claim 1 wherein said blow plug blocks said first rearward opening and said blow plug is displaceable, so as to unblock said fluid passage, under pressure of a liquid component contained in one of said compartments, as induced by forward movement of the plunger, said liquid containing compartment being disposed between the plunger and said rearward axial end wall.

3. A syringe assembly as defined in claim 2, wherein catch means, for the retention of said blow plug, is disposed within said bypass chamber about the second forward opening.

4. A syringe assembly as defined in claim 3, wherein the blow plug has a frusto-conical shape, a concave rearward face and a forward conical base disposed on the bypass chamber interior side of the rearward axial end wall.

5. A syringe assembly as defined in claim 3, wherein the blow plug is a uniform disk.

6. A syringe assembly as defined in claim 2, wherein the blow plug has a concave rearward face.

7. A syringe assembly as defined in claim 2, wherein the blow plug has a frusto-conical shape, a concave rearward face and a forward conical base disposed on the bypass chamber interior side of the rearward axial end wall.

8. A syringe assembly as defined in claim 2, wherein the blow plug is a uniform disk.

9. A syringe assembly as defined in claim 2, wherein said second forward opening is laterally offset with respect to the first rearward opening.

* * * * *